United States Patent [19]

Flam

[11] Patent Number: 5,607,386
[45] Date of Patent: Mar. 4, 1997

[54] MALLEABLE FIBEROPTIC INTUBATING STYLET AND METHOD

[76] Inventor: Gary H. Flam, 2244 Robinhood, Houston, Tex. 77005

[21] Appl. No.: 402,367

[22] Filed: Mar. 13, 1995

Related U.S. Application Data

[63] Continuation-in-part of Ser. No. 124,016, Sep. 21, 1993, Pat. No. 5,431,152.

[51] Int. Cl.$^6$ ........................................................ A61B 1/04
[52] U.S. Cl. ........................ 600/120; 600/114; 600/194; 128/200.26; 128/912; 128/DIG. 26
[58] Field of Search .................................... 600/120, 131, 600/114, 115, 116, 182, 190, 188, 194, 197; 128/200.26, 911, 912, DIG. 26, 207.14; 604/117, 164, 165, 166, 280, 281, 264

[56] References Cited

U.S. PATENT DOCUMENTS

| | | | |
|---|---|---|---|
| 4,696,544 | 9/1987 | Costella | 600/114 X |
| 5,237,881 | 6/1994 | Greene | 600/120 |

Primary Examiner—Richard J. Apley
Assistant Examiner—Beverly M. Flanagan
Attorney, Agent, or Firm—Kenneth A. Roddy

[57] ABSTRACT

A malleable fiberoptic intubating apparatus has an elongate arcuate thin-walled tubular stylet which removably carries an endotracheal tube around it and the fiberoptic bundle of a flexible fiberoptic bronchoscope within it, a handle at the rearward end of the stylet, and a telescoping bronchoscope support arm that releasably receives and carries a bronchoscope and moves relative to the handle. An adjustable endotracheal tube positioning element engages the proximal end of the endotracheal tube and positions it on the stylet. An adjustable fiberoptic bundle positioning element engages the flexible fiberoptic bundle of the bronchoscope and positions it within the stylet. The instrument is placed in the mouth, the larynx is identified, and the instrument is advanced as a unit into the trachea. Then the fiberoptic bronchoscope and stylet are removed from the mouth, leaving the endotracheal tube in the proper part of the trachea.

21 Claims, 5 Drawing Sheets

MALLEABLE FIBEROPTIC INTUBATING STYLET AND METHOD

CROSS REFERENCE TO RELATED APPLICATION

This application is a continuation in part of U.S. patent application Ser. No. 08/124,016 filed Sep. 21, 1993, now U.S. Pat. No. 5,431,152.

BACKGROUND OF THE INVENTION

1. Field of the Invention

This invention relates generally to medical instruments and fiberoptic intubating apparatus, and more particularly to a malleable fiberoptic intubating apparatus having a hollow, thin-walled stylet which removably carries an endotracheal tube around it and the fiberoptic bundle of a flexible fiberoptic bronchoscope within it, a handle, and a telescoping bronchoscope support arm that receives and carries a bronchoscope.

2. Brief Description of the Prior Art

Endotracheal intubation is a medical procedure which concerns placement of a tube in the trachea of a patient to facilitate breathing or to permit the controlled introduction of gasses through the tube by an anesthesiologist or other medical personnel. Endotracheal intubation is normally carried out after induction of anesthesia or in emergencies, and is usually accomplished without great difficulty under direct vision with a laryngoscope by the anesthesiologist. The laryngoscope is an instrument used to examine the larynx (the uppermost end of the trachea narrowed by two surrounding vocal cords and located below the root of the tongue).

With direct laryngoscopy, the patient's neck is flexed, the head is extended and the mouth is opened wide. A laryngoscope having a rigid straight blade (commonly known as a Miller-type blade), or a rigid curved blade (commonly known as a Macintosh-type blade) is placed along the right side of the tongue, and the tongue and soft tissues of the mouth are retracted anteriorly and inferiorly to enable the larynx to be seen directly through the mouth in a straight line, instead of the normal anatomic curve around the tongue from the mouth to the larynx. The endotracheal tube is then placed directly into the trachea, along this direct line of vision.

Occasionally, the anesthesiologist is unable to visualize the larynx using traditional direct laryngoscopy methods in a patient who has no history or signs by physical examination of being a difficult intubation. For example, many patients have decreased mobility of the head and neck, protruding upper teeth, limited mouth opening, abnormally large or small mandibles, large tongues, tumors in the oropharynx or larynx, or trauma to the face and neck, all of which prevent direct visualization for intubation of the larynx and trachea. These types of patients are usually intubated while awake and through the nose blindly or via fiberoptic endoscopy so that an open protected airway can be maintained by the patient until it is secured by the anesthesiologist. Blind endotracheal intubation has inherent disadvantages; for example, stylets, obturators, or other guides can injure the patient, and there is no visual evidence that the endotracheal tube has correctly entered the trachea.

Direct laryngoscopy requires mouth opening and head and neck positioning that may be impossible or injurious to a patient with head or neck trauma. The larynx may never be able to be identified, or the endotracheal tube may not be able to be passed through it, even if it is identified. There is usually no means for oxygen delivery or suctioning during laryngoscopy.

Rigid fiberoptic laryngoscopy will aid in locating the larynx, but it is frequently difficult to guide the endotracheal tube into the trachea without rigid stylets or other guides, which may damage the soft tissues of the head and neck. Potential obstruction of the light source or field of view by the tube itself, secretions, blood, or soft tissues, and inability to confirm proper final tube position in the trachea are inherent drawbacks.

Flexible fiberoptic bronchoscopy faces difficulty in penetration through soft tissues in search of the larynx, because of its lack of stiffness, as well as obstruction of the field of view by soft tissues, secretions, or blood. Presently, oral intubation with a flexible fiberoptic bronchoscope requires a special hollow airway which is fixed in shape. Once the fiberoptic bronchoscope is passed beyond the tip and into the oropharynx in search of the larynx, it has no protection from secretions, and no support or retraction to allow it to easily pass through the soft tissues and into the larynx. The same problem exists for nasal flexible fiberoptic intubation. It is also impossible to use this instrument with just one hand.

While malleable fiberoptic intubating stylets have been around for quite some time (i.e., since the late 1970's), they have some distinct disadvantages. First, there is frequently no flexibility of the end portion, so the passage of the instrument deep into the trachea for inspection of final tube placement can result in stylet produced injury. Second, if the endotracheal tube and contained fiberoptic bundles cannot be passed through the vocal cords together (i.e., because the tube tip continues to abut against the right vocal cord), the safest and most effective way around this is to atraumatically pass a completely flexible fiberoptic bundle first into the trachea to act as a guide, and then pass the endotracheal tube in over it. Third, the malleable fiberoptic stylet offers no way to handle the tube with contained bronchoscope tubing independently from the viewing portion and then couple them together, as one unit, when desired for ease of use. Fourth, the conventional malleable fiberoptic stylets are prohibitive in cost, in the over $1,000 range. The present malleable fiberoptic intubating stylet overcomes the above described problems.

There are several patents which disclose various fiberoptic intubating stylets and instruments used for laryngoscopy and endotracheal intubation.

Rassoff, U.S. Pat. No. 5,183,031; Adair, U.S. Pat. No. 5,329,940; and Salerno, U.S. Pat. No. 5,337,735 disclose malleable fiberoptic intubating stylets with intrinsic endoscope portions that are fixed in place within the devices. They cannot be manipulated independently from the rest of the device, nor can they pass alone into the trachea. This severely limits their use.

Greene, U.S. Pat. No. 5,327,881 discloses another fiberoptic intubating stylet in which the endoscope is also intrinsic to the device. Although it does have a flexible portion, the other portions are more rigid, which may cause damage to the structure of the larynx and trachea.

Harvey, U.S. Pat. No. 5,279,281 discloses a flexible laryngoscope with a directing mechanism that positions the fiberoptic cable at a substantially 90° angle from the laryngoscope body and a guide mechanism for controlling the location of the free end of the fiberoptic cable. As with the the previously described stylets, the endoscope head (viewing portion) and device with the endotracheal tube cannot be manipulated separately. There is also no ability for axial positioning and movement of the endoscope through the endotracheal tube. Also, the 90° turn can cause bending and rotation of the fiberscope which can damage the delicate optical fibers.

Frankel, U.S. Pat. No. 4,793,327 discloses a blind intubation device which consists of an airway opening device which is inserted into the patient's mouth and adjusted to a fixed position to hold the mouth open while an automatic intubation guide is inserted for guiding an endotracheal tube into the trachea. The airway opening device has an opening through which the guide is fed into the mouth. An endotracheal tube is also fed through the airway opening device and by means of an adapter or track on the guide, the endotracheal tube is inserted into the trachea, after which the guide is withdrawn and the airway opening device is retracted from its fixed position and removed from the mouth.

Fletcher, U.S. Pat. No. 4,329,983 discloses a guide device for endotracheal tubes which includes a flexible bar that is inserted into the endotracheal tube and has a flexible line which extends along the bar and is manipulated to flex the bar in bowed fashion against the endotracheal tube to urge the tube forwardly toward the trachea and away from the esophagus. It can be used along with direct laryngoscopy in difficult patients to help facilitate passage of the endotracheal tube through the larynx.

Phillips, U.S. Pat. No. 3,856,001 discloses a rigid laryngoscope blade having a straight portion and a curved portion with a longitudinal channel for passing an endotracheal tube. An electrical lamp is secured on one side of the blade at the forward end of the straight portion and aimed inwardly and downwardly and electrical wires extend from the lamp to the handle, which contains a power source.

Bullard, U.S. Pat. No. 4,086,919 discloses a rigid fiberoptic laryngoscope having a curved blade with a connection member at the proximal end for connection to a laryngoscope handle and an eyepiece that extends outwardly from the blade at the proximal end. Fiberoptic bundles extend along the longitudinal axis of the blade and terminate at the end of the blade. An endotracheal tube may be passed beneath the blade, alongside the fiberoptic bundle into the trachea.

Lowell, U.S. Pat. No. 4,306,547 discloses a rigid fiberoptic laryngoscope having a forwardly extending blade and a tube supporting channel. A viewing assembly and light source are each connected to fiberoptic bundles which extend longitudinally through the length of the top wall and terminate at the open end of the channel.

Wu, U.S. Pat. No. 4,982,729 discloses a rigid fiberoptic laryngoscope having an integral handle and curved blade with fiberoptic bundles which extend longitudinally through the length of the blade and terminate at the end of the blade. A bivalve element is releasably attachable to the blade to form a passageway for threading an endotracheal tube through the distal end of the blade.

Augustine, U.S. Pat. No. 5,203,320 discloses a rigid tubular contoured fiberoptic tracheal intubation guide having a through bore for holding an endotracheal tube. Correct positioning of the device is detected by external palpation of the neck of the patient and tracheal intubation is confirmed with fiberoptic visualization.

MacAllister, U.S. Pat. No. 5,016,614 discloses an endotracheal intubation apparatus having a handle and mechanism for retaining an endotracheal tube on an elongated obturator element extending from the handle and releasing the endotracheal tube therefrom. The obturator element accommodates an endoscope therethrough to permit visualization at the end thereof.

Parker, U.S. Pat. No. 5,038,766 discloses a disposable, one-piece, contoured guide element having a channel therethrough which is releasably mounted at the end of a curved blade and handle. The device is used for blindly guiding and aiming orolaryngeal and oroesophogeal tubular members.

The present invention is distinguished over the prior art in general, and these patents in particular by a malleable fiberoptic intubating apparatus that has an elongate arcuate thin-walled tubular stylet which removably carries an endotracheal tube around it and the fiberoptic bundle of a flexible fiberoptic bronchoscope within it, a handle at the rearward end of the stylet, and a telescoping bronchoscope support arm that releasably receives and carries a bronchoscope and moves relative to the handle. An adjustable endotracheal tube positioning element engages the proximal end of the endotracheal tube and positions it on the stylet. An adjustable fiberoptic bundle positioning element engages the flexible fiberoptic bundle of the bronchoscope and positions it within the stylet. The instrument is placed in the mouth, the larynx is identified, and the instrument is advanced as a unit into the trachea. Then the fiberoptic bronchoscope and stylet are removed from the mouth, leaving the endotracheal tube in the proper part of the trachea.

SUMMARY OF THE INVENTION

It is therefore an object of the present invention to provide a malleable fiberoptic intubating stylet and method which can be used to facilitate rapid, successful, and nonlethal oral endotracheal intubation of both awake and unconscious patients.

It is another object of the present invention to provide a malleable fiberoptic intubating stylet which can be used as a laryngoscope and to intubate the trachea either when the traditional and other laryngoscopes have failed, or when they cannot be used for various reasons.

Another object of this invention to provide a malleable fiberoptic intubating apparatus and method which reduces the amount of pressure against the upper teeth, tongue and other soft tissues in the head and neck during laryngoscopy.

Another object of this invention is to provide a malleable fiberoptic intubating stylet and method which allows minimal mouth opening and minimal manipulation of the head and neck during intubation and laryngoscopy.

Another object of this invention is to provide a malleable fiberoptic intubating stylet which has a malleable hollow tubular stylet that carries the flexible fiberoptic bundle of a fiberoptic bronchoscope within it, while acting as a rigid guide for carrying an endotracheal tube around it, to pass through the soft tissues of the mouth to reach the larynx.

Another object of this invention is to provide a malleable fiberoptic intubating stylet which carries the flexible fiberoptic bundle of a fiberoptic bronchoscope within it and an endotracheal tube around it, and allows independent manipulation of the endotracheal tube and the viewing portion of the bronchoscope.

Another object of this invention is to provide a malleable fiberoptic intubating stylet which has a telescoping fiberscope support arm which releasably receives and carries a bronchoscope and moves relative to the handle and allows engagement of the viewing portion to the handle so that the whole apparatus can be removed from the mouth with one hand as the endotracheal tube is held in place with the other.

Another object of this invention is to provide a malleable fiberoptic intubating stylet for visualization and intubation of the trachea that has a flexible viewing portion and an external light source, both of which minimize risks of trauma or burn injury to the patient.

Another object of this invention is to provide a malleable fiberoptic intubating stylet and method which allows continuous manipulation of the endotracheal tube in an unchanging fixed position within the field of view, and subsequent confirmation of placement of the tube in the desired part of the trachea.

Another object of this invention is to provide a malleable fiberoptic intubating stylet that can be used for intubation with a continuous illuminated field of view during the whole process of endotracheal intubation, from beginning to end.

Another object of this invention is to provide a malleable fiberoptic intubating stylet that protects the illuminated field of view of from obstruction by soft tissues, secretions or blood throughout the whole process of endotracheal intubation.

A further object of this invention is to provide a malleable fiberoptic intubating stylet that allows both oxygen insufflation to the patient and suction to enhance visualization and help preclude lethal aspiration of vomitus during laryngoscopy and intubation.

A still further object of this invention is to provide a malleable fiberoptic intubating stylet which is simple in construction, compact, inexpensive to manufacture, and can rapidly be used in any emergency situation with minimal preparation.

Other objects of the invention will become apparent from time to time throughout the specification and claims as hereinafter related.

The above noted objects and other objects of the invention are accomplished by a malleable fiberoptic intubating apparatus that has an elongate arcuate thin-walled tubular stylet which removably carries an endotracheal tube around it and the fiberoptic bundle of a flexible fiberoptic bronchoscope within it, a handle at the rearward end of the stylet, and a telescoping bronchoscope support arm that releasably receives and carries a bronchoscope and moves relative to the handle. An adjustable endotracheal tube positioning element engages the proximal end of the endotracheal tube and positions it on the stylet. An adjustable fiberoptic bundle positioning element engages the flexible fiberoptic bundle of the bronchoscope and positions it within the stylet. The instrument is placed in the mouth, the larynx is identified, and the instrument is advanced as a unit into the trachea. Then the fiberoptic bronchoscope and stylet are removed from the mouth, leaving the endotracheal tube in the proper part of the trachea.

DESCRIPTION OF THE PREFERRED EMBODIMENT

Figures 1, 2:
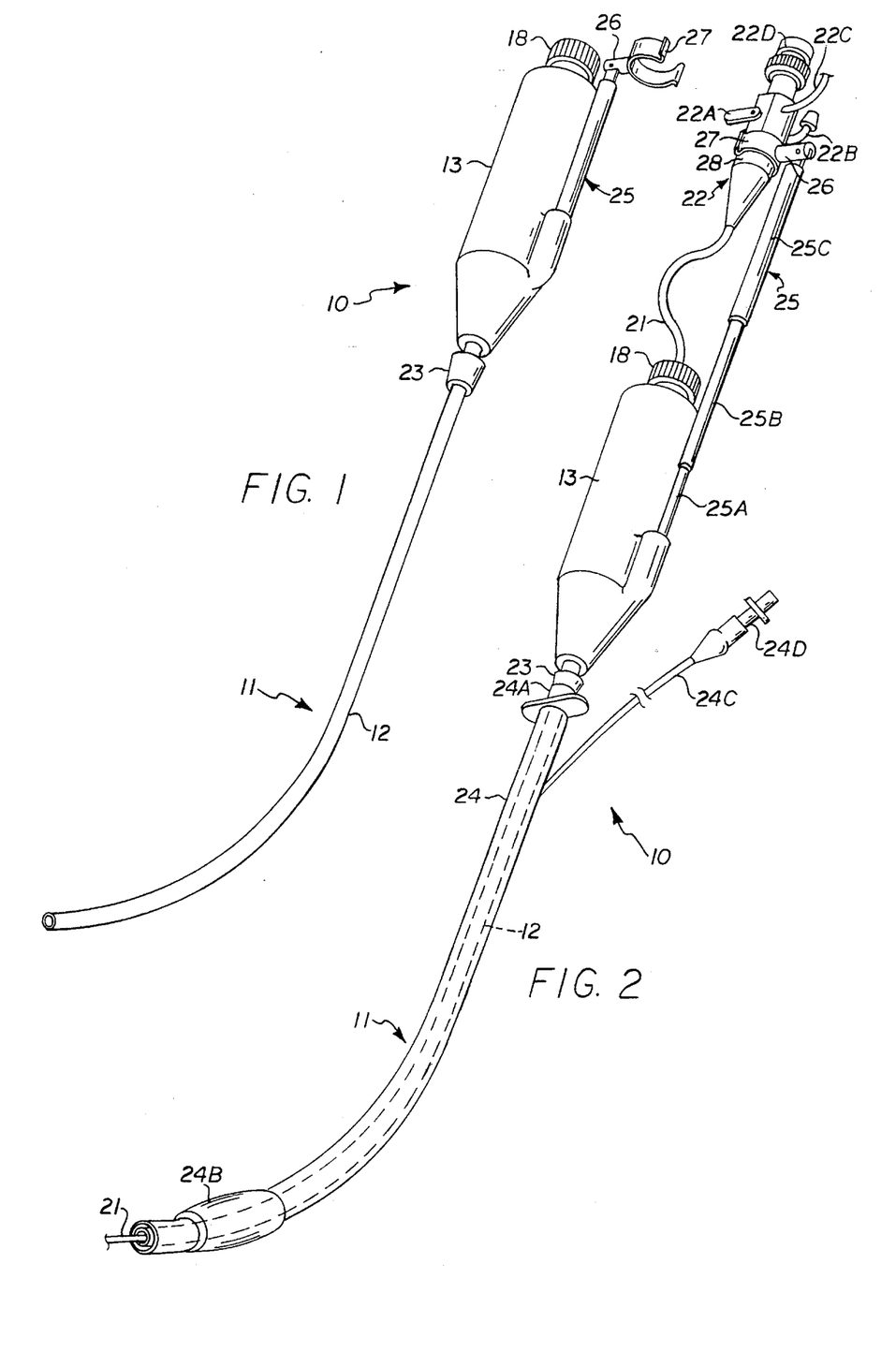
FIG. 1 is a perspective view of a preferred embodiment of the malleable fiberoptic intubating stylet in accordance with the present invention.
FIG. 2 is a perspective view of the malleable fiberoptic intubating stylet having a cuffed endotracheal tube and a fiberoptic bronchoscope installed thereon, showing the telescopic bronchoscope support arm in an extended position.

Referring now to the drawings by numerals of reference, a preferred malleable fiberoptic intubating stylet instrument in accordance with the present invention is designated as numeral 10. As seen in FIGS. 1 and 2, the forward or distal portion 11 of the device is a thin-walled tubular conduit or stylet 12 formed of stiff malleable material which is longitudinally arcuate in shape to match the generally C-shaped curve of the oropharynx along the surface of the tongue of a patient. The stylet 12 is at least 26 cm in length to accommodate any cut oral endotracheal tube length (described hereinafter).

Figure 3:
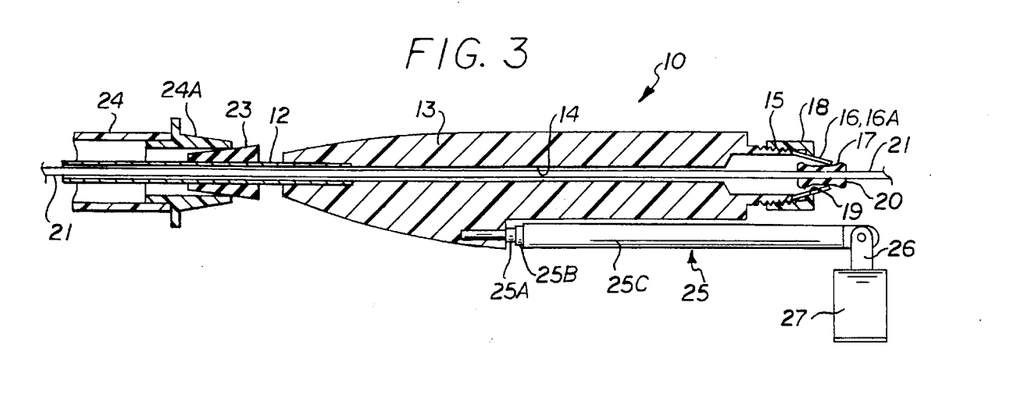
FIG. 3 is a longitudinal cross section through the handle portion of the malleable fiberoptic intubating stylet.

As best seen in FIG. 3, the rear or proximal end of the stylet 12 is secured within a handle 13. The handle 13 is a generally cylindrical member of sufficient dimension to comfortably fit into the hand of the operator and has a conical forward end. The handle 13 has a central bore 14 of a diameter equal to or slightly larger than the interior diameter of the tubular stylet 12.

The rearward or proximal end of the handle 13 has a reduced diameter externally threaded portion 15 terminating in an inwardly tapered conical male portion 16 having radial circumferentially spaced slots 16A and a central bore 17. An end cap 18 having internal threads and a central bore 19 is threadedly received on the conical male portion of the handle and when tightened thereon will compress the segmented conical portion of the handle inwardly. A small tubular sleeve or bronchoscope positioning element 20 formed of resilient material has a central bore sized to frictionally receive the fiberoptic bundle 21 of a fiberoptic bronchoscope 22 and its exterior is sized and shaped to fit into the bore of the segmented conical portion 16 of the handle to prevent compression damage to the fiberoptic bundle. The exterior of the resilient sleeve or positioning element 20 may be tapered outwardly toward each end to maintain it in the bore of the conical male portion. The bronchoscope positioning element 20 frictionally engages the fiberoptic bundle 21 and allows it to move only when axial force or tension is applied to the bundle.

Alternatively, the rear end of the handle 13 may have a reduced diameter bore which carries a small washer of resilient material having a central bore which is sized to frictionally receive the fiberoptic bundle of the fiberoptic bronchoscope and serves as the bronchoscope positioning element.

A conical endotracheal tube attachment and positioning member 23 formed of resilient material is frictionally positioned on the rearward portion of the stylet 12. The tapered exterior of the endotracheal tube attachment and positioning member 23 allows frictional engagement of the rearward portion of a standard endotracheal tube 24 or tube connector 24A. The interior bore of the endotracheal tube attachment and positioning member 23 is slightly smaller than the exterior diameter of the stylet 12 to provide frictional engagement thereon and to allow the attachment and positioning member 23 to be adjustably positioned along the length of the stylet.

Figure 4:
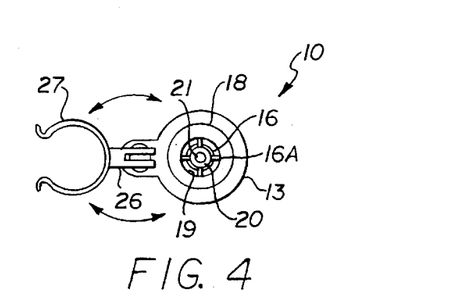
FIG. 4 is a proximal end view of the handle portion of the malleable fiberoptic intubating stylet.

A telescoping tubular bronchoscope support arm 25 is secured at its forward end to one side of the handle 13 parallel to the longitudinal axis of the handle. The rear end of the telescoping tubular bronchoscope support arm 25 has a short section 26 hinged thereto which extends laterally outward to one side and has a generally C-shaped clip 27 secured to its outer end to receive the tubular head portion 28 of the fiberoptic bronchoscope 22. The clip 27 may be coated with a resilient material to facilitate gripping the bronchoscope head. The telescoping tubular sections 25A, 25B, 25C of the support arm 25 may be extended and collapsed longitudinally relative to the handle 13 and the laterally extending section 26 and clip 27 can be rotated about the longitudinal axis of the telescoping support arm 25. The center of the C-shaped clip 27 is oriented such that it can be centered along the central axis of the handle 13, or can be rotated 180° away from the handle axis as shown in FIG. 4.

Figure 5:
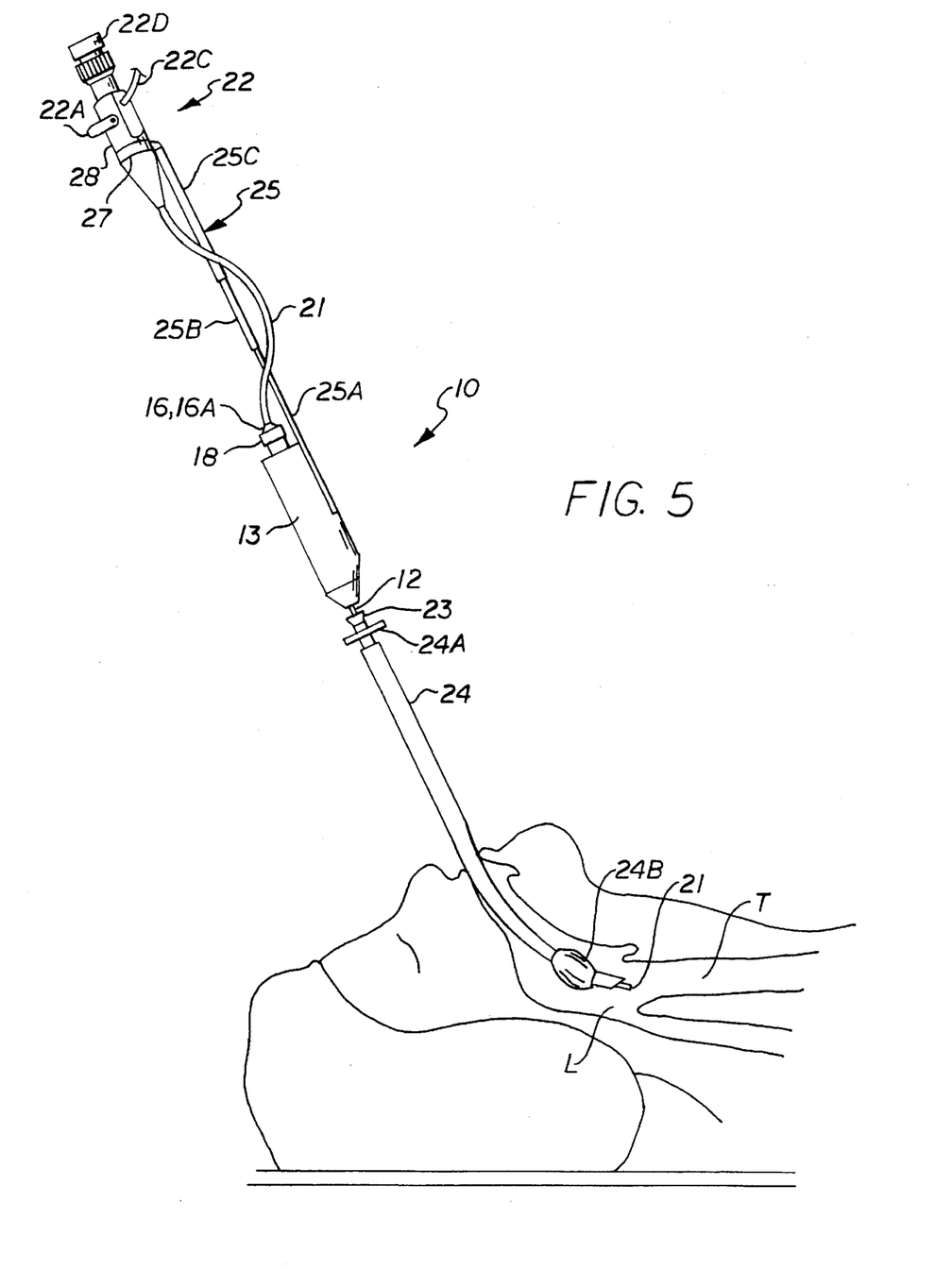
FIG. 5 is a side view in partial cross section showing the assembled fiberoptic intubating stylet in the mouth of a patient.

In the collapsed position (FIGS. 1 and 3) of the support arm 25, the C-shaped clip 27 is spaced closely adjacent the rear end of the handle 13. When the support arm 25 is extended (FIGS. 2 and 5) the clip 27 is positioned a sufficient distance from the rear end of the handle 13 to support the head of the fiberoptic bronchoscope 22 and allow manual feeding of the fiberoptic bundle 21 (using one hand) to a point just above the right and left bronchial openings, and thus confirm the tube position (approx. 10").

The endotracheal tube 24 and flexible fiberoptic bronchoscope 22 are of conventional construction, and therefore, not shown in detail. The preferred endotracheal tube 24 has a standard size connector 24A at its rearward end and an inflatable cuff 24B surrounding its distal end which is inflated by means of the usual small diameter air injection tube 24C connected with the inflatable cuff and provided with a connector 24D at its proximal end for inflating the cuff. The preferred flexible fiberoptic bronchoscope 22 has an external light source, tip control lever 22A, and ports 22B on the head 28 of the scope for 02 insufflation or medicine insufflation and suction. The bronchoscope 22 is connected by a fiberoptic cable 22C to a light source (not shown), and has an eyepiece 22D at its outer end.

The bronchoscope 22 may also be provided with a longitudinal insufflation an vacuum lumen (not shown) which extends along its length and terminates at the tip at the forward or distal end of the fiberoptic bundle which is connected via the port 22B to a source of vacuum or oxygen which allows the operator to apply suction or insufflation at the tip of the fiberoptic bundle. Alternatively, the bronchoscope 22 may also be connected to a display screen for displaying the image seen through the fiberoptic bundle.

OPERATION

To assemble the malleable fiberoptic intubating stylet 10 for use (FIGS. 2 and 3), the flexible fiberoptic bundle 21 of the fiberoptic bronchoscope 22 is passed through the resilient bronchoscope positioning element 20 at the rear end of the handle 13 and through the stylet 12 until its tip reaches a point just behind the forward end of the stylet. Then the end cap 18 is tightened to secure the fiberoptic bundle in the proper position within the stylet. A standard endotracheal tube 24 cut to about 25 cm or less is then installed over the stylet 12 from the forward end and its connector piece 24A at the rearward end is pressed onto the resilient conical endotracheal tube attachment and positioning member 23 positioned on the rearward portion of the stylet. The resilient endotracheal tube attachment and positioning member 23 keeps the endotracheal tube 24 positioned on the stylet 12 so that the front end of the tube is just beyond the forward end of the stylet.

The head 28 of the fiberoptic bronchoscope 22 is clipped into the upwardly extended bronchoscope support arm clip 27. The assembled device is placed in the mouth with the left hand. The assembly can be manipulated as a single unit, or the bronchoscope can be held with the right hand while the rest of the assembly is manipulated with the left hand. After appropriate manipulation, the larynx L is identified, and the endotracheal tube 24, stylet 12, and fiberoptic bundle 21 are placed through it and into the trachea T. In an awake patient, local anesthetic can be sprayed through the bronchoscope channel onto and through the larynx to minimize coughing and discomfort from the intubation.

The field of view seen through the eyepiece 22D (or display screen) begins just rearward or proximal to the forward or distal end of the endotracheal tube 24. The distal end of the endotracheal tube 24 and stylet 12 surrounding the fiberoptic bundle 21 provide protection of the visual field from obstruction by soft tissues, blood or secretions.

Figure 6:
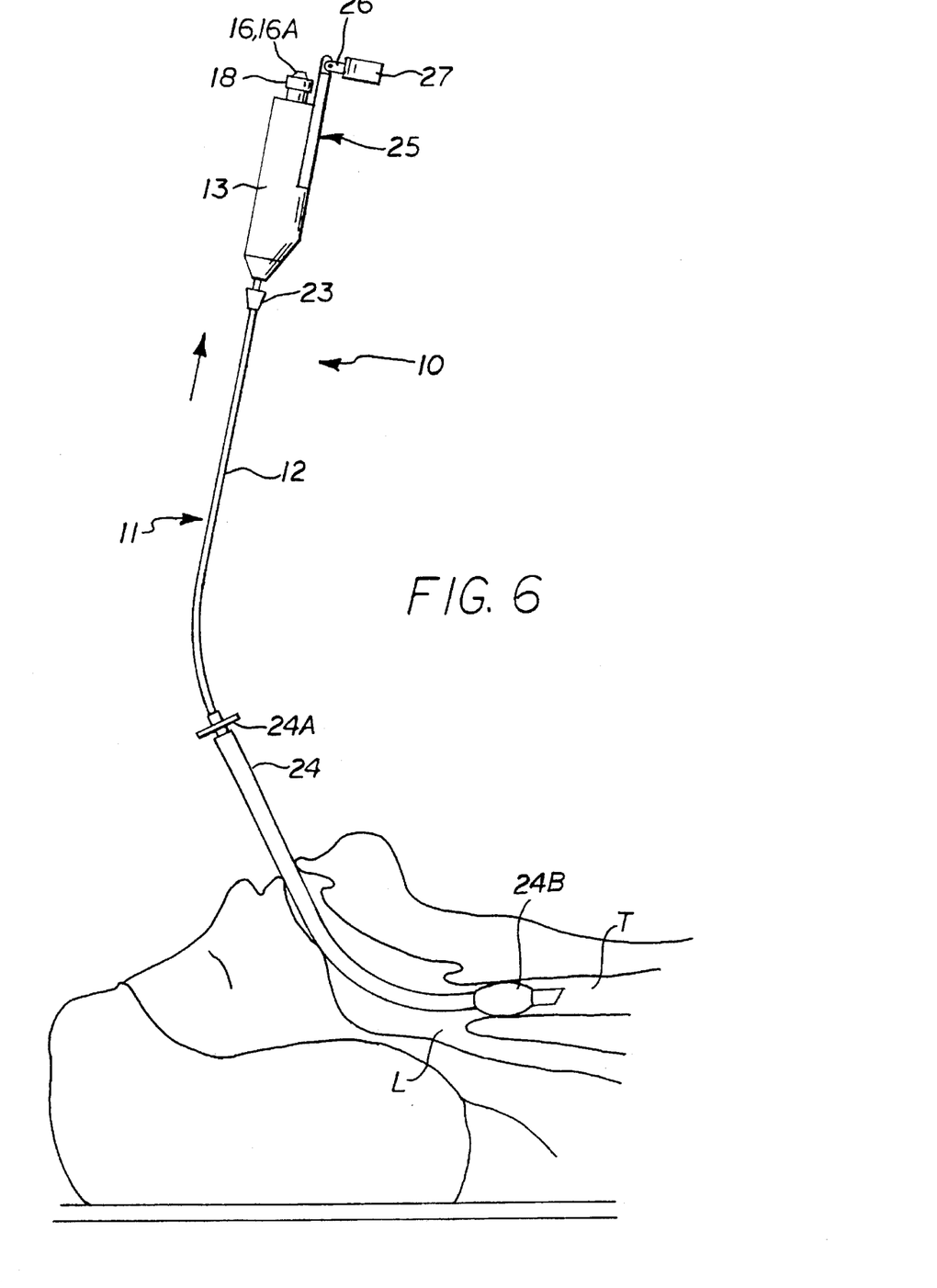
FIG. 6 is a side view in partial cross section showing the bronchoscope removed from the fiberoptic intubating stylet and the fiberoptic intubating stylet being withdrawn from the endotracheal tube which has been placed in the trachea of the patient.

After the endotracheal tube 24 has been properly placed, the endotracheal tube is held with the right hand, as the stylet and fiberoptic bronchoscope are removed from the mouth as a single unit with the left hand, or alternatively, as shown in FIG. 6, the fiberoptic bronchoscope 22 can be removed, followed by the stylet 12, leaving the endotracheal tube 24 in proper position.

If unable to pass the endotracheal tube, stylet, and fiberoptic bundle together into the trachea, or if a deeper view of the trachea is desired, the head of the fiberoptic bronchoscope can be clipped to the clip at the end of the upwardly extended support arm. This frees up the left hand which can then be used to feed the excess length of the fiberoptic bundle into the trachea (after loosening the bronchoscope positioning element end cap). The endotracheal tube can be slid along the fiberoptic bundle as needed, and positioned appropriately. Then, the entire instrument is removed with the left hand as the right hand secures the endotracheal tube in the desired position.

Because the tip of the fiberoptic bundle 21 is inside the tubular stylet 12, and also protected by the endotracheal tube 24, the present intubating stylet instrument provides a continuous unobstructed illuminated field of view. It allows continuous manipulation of the endotracheal tube in an unchanging fixed position within the field of view, and subsequent confirmation of placement of the tube in the desired part of the trachea, and it protects the illuminated field of view from soft tissues, secretions or blood throughout the whole process of endotracheal intubation.

DESCRIPTION OF ANOTHER PREFERRED EMBODIMENT

Figures 7, 8:
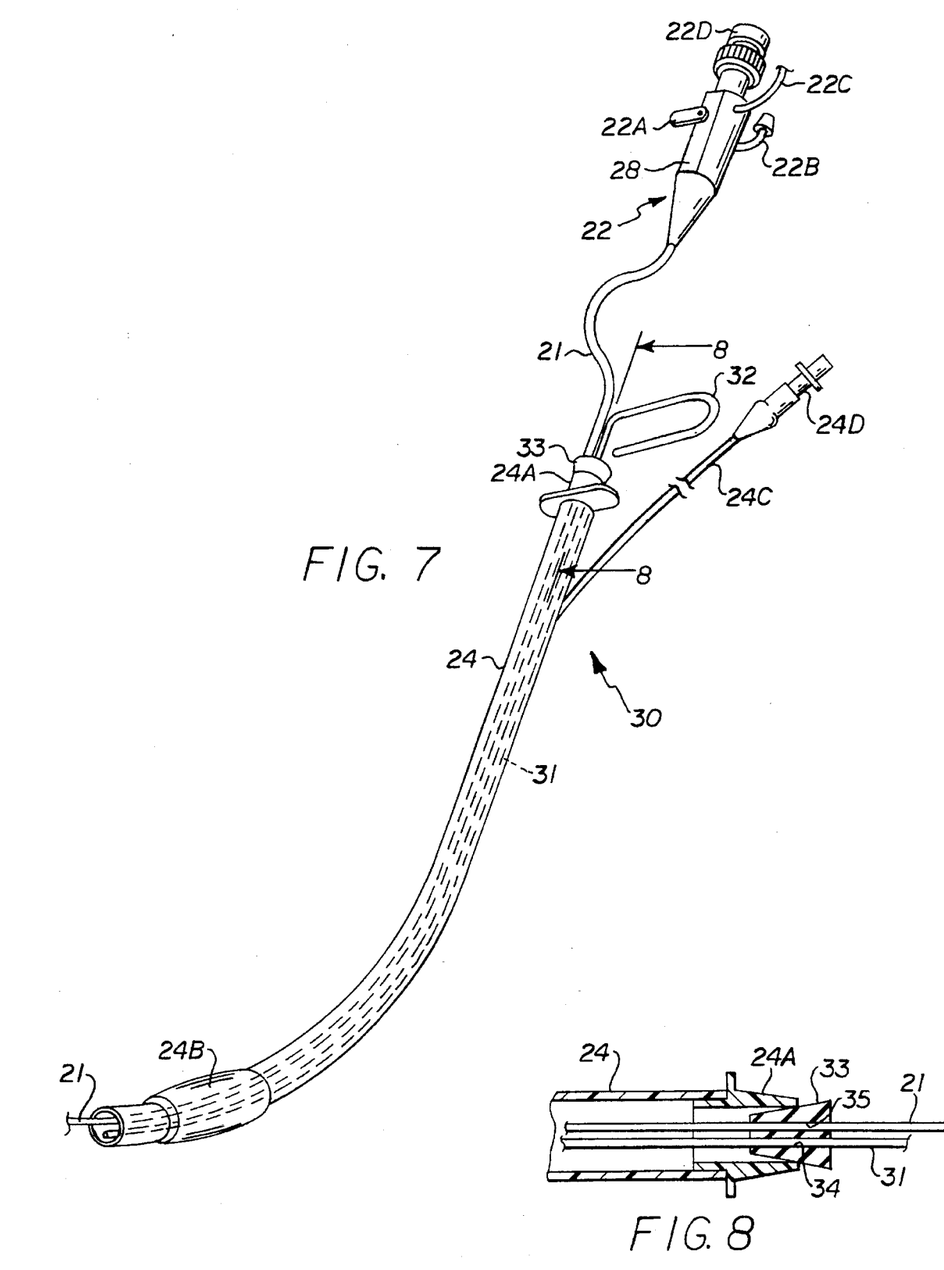
FIG. 7 is a perspective view of a second preferred embodiment of the malleable fiberoptic intubating stylet in accordance with the present invention.
FIG. 8 is a longitudinal cross section through the rear portion of the malleable fiberoptic intubating stylet, taken along line 8—8 of FIG. 7.

Referring now to FIGS. 7 and 8, another preferred malleable fiberoptic intubating stylet instrument in accordance with the present invention is designated as numeral 30. The instrument 30 has a length of malleable wire or stylet 31 which may be formed into a longitudinally arcuate configuration to match the generally C-shaped curve of the oropharynx along the surface of the tongue of a patient. The rear or proximal end of the wire 31 is bent into a loop to form a handle 32 which can be comfortably gripped by the hand of the operator.

A conical endotracheal tube attachment and positioning member 33 formed of resilient material is frictionally positioned on the rearward portion of the wire 31 adjacent the handle portion 32 by passing the wire through a first bore 34 in the member 33. The tapered exterior of the endotracheal tube attachment and positioning member 33 allows frictional engagement of the rearward portion of a standard endotracheal tube 24 or tube connector 24A. The bore 34 of the endotracheal tube attachment and positioning member 33 is slightly smaller than the exterior diameter of the wire 31 to provide frictional engagement thereon and to allow the attachment and positioning member 33 to be adjustably positioned along the length of the wire. When the endotracheal tube 24 is received over the wire 31, the wire gives rigidity to the endotracheal tube 24 to facilitate manual manipulation.

The conical endotracheal tube attachment and positioning member 33 is provided with a second bore 35 extending therethrough parallel to the first bore 34 which is sized to frictionally receive the fiberoptic bundle 21 of a fiberoptic bronchoscope 22. The second bore 35 frictionally engages the fiberoptic bundle 21 and allows it to move only when axial force or tension is applied to the bundle and serves as a bronchoscope positioning element.

The endotracheal tube 24 and flexible fiberoptic bronchoscope 22 are of conventional construction, and therefore, not shown in detail. As previously described, the preferred endotracheal tube 24 has a standard size connector 24A at its rearward end and an inflatable cuff 24B surrounding its distal end which is inflated by means of the usual small diameter air injection tube 24C connected with the inflatable cuff and provided with a connector 24D at its proximal end for inflating the cuff. The preferred flexible fiberoptic bronchoscope 22 has a generally tubular head portion 28, an external light source, tip control lever 22A, and ports 22B on the head of the scope for $O_2$ insufflation or medicine insufflation and suction. The bronchoscope 22 is connected by a fiberoptic cable 22C to a light source (not shown), and has an eyepiece 22D at its outer end.

The bronchoscope 22 may also be provided with a longitudinal insufflation an vacuum lumen (not shown) which extends along its length and terminates at the tip at the forward or distal end of the fiberoptic bundle which is connected via the port 22B to a source of vacuum or oxygen which allows the operator to apply suction or insufflation at the tip of the fiberoptic bundle. Alternatively, the bronchoscope 22 may also be connected to a display screen for displaying the image seen through the fiberoptic bundle.

In the embodiment of FIGS. 7 and 8, the proximal end of the endotracheal tube 24 or the handle portion 32 of the wire 31 is held in one hand, and the head 28 of the fiberoptic bronchoscope 22 is held in the other hand, and intubation is performed as described above.

While this invention has been described fully and completely with special emphasis upon preferred embodiments, it should be understood that within the scope of the appended claims the invention may be practiced otherwise than as specifically described herein.

I claim:

1. A fiberoptic intubating stylet instrument for oral fiberoptic endotracheal intubation comprising in combination:

a generally cylindrical handle configured to fit into the hand of an operator and having a forward end, a rearward end, and a central longitudinal bore;

a fiberoptic bundle positioning means at the rearward end of said handle;

a tubular telescoping fiberoptic scope support arm on said handle having releasable mounting means at an outer end for releasably mounting a fiberoptic scope thereon;

an elongate curvilinear hollow tubular stylet having a rearward end secured to said handle, a forward tip end, and a longitudinal channel extending therethrough coextensive with said handle central bore;

a fiberoptic scope releasably mounted on said support arm mounting means and having viewing means connected at a rearward end and an elongate thin flexible fiberoptic bundle which transmits light and visual images extending forwardly therefrom and terminating in a tip end and having a midsection therebetween, said fiberoptic bundle passing slidably through said fiberoptic bundle positioning means, said handle central bore and said stylet longitudinal channel;

endotracheal tube attachment and positioning means movably mounted on said stylet configured to removably engage the rearward end of an endotracheal tube and releasably maintain the endotracheal tube in a surrounding condition on said stylet;

a flexible endotracheal tube having a rearward end removably engaged on said endotracheal tube attachment and positioning means, an interior diameter surrounding said stylet when engaged thereon, and a forward tip end;

said endotracheal tube attachment and positioning means being selectively movable on said stylet for adjustably positioning and maintaining said forward tip end of said endotracheal tube relative to said forward tip end of said stylet; and said fiberoptic bundle positioning means being engaged with said fiberoptic bundle to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

2. The fiberoptic intubating stylet instrument according to claim 1 in which said tubular stylet is malleable along its length and capable of being manually formed to pass through the mouth and into the larynx of the particular patient into which the endotracheal tube is to be placed.

3. The fiberoptic intubating stylet instrument according to claim 1 in which said tubular telescoping fiberoptic scope support arm is selectively adjustable in length along its longitudinal axis and said releasable mounting means at the outer end thereof is rotatable about said longitudinal axis.

4. The fiberoptic intubating stylet instrument according to claim 1 in which said endotracheal tube attachment and positioning means comprises a resilient member having a central aperture frictionally and slidably engaged on the exterior of said stylet to allow said endotracheal tube engaged thereon to slide longitudinally relative thereto upon the application of sufficient axial force relative to one another.

5. The fiberoptic intubating stylet instrument according to claim 4 in which said resilient member has an exterior surface configured to frictionally engage either the rearward end of said endotracheal tube or a standard endotracheal tube connector installed in the rearward end of an endotracheal tube, and to allow disengagement and disconnection of said endotracheal tube or said endotracheal tube having a standard endotracheal tube connector installed in the rearward end thereof upon the application of sufficient axial force relative to one another.

6. The fiberoptic intubating stylet instrument according to claim 1 in which said fiberoptic bundle positioning means comprises a resilient member having a central aperture through which said fiberoptic bundle passes and is frictionally and slidably engaged therewith to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

7. The fiberoptic intubating stylet instrument according to claim 6 further comprising adjustable tightening means surrounding said fiberoptic bundle positioning means resilient member to selectively apply a radial force thereto such that said resilient member firmly grips said fiberoptic bundle to maintain it in a selected position.

8. A fiberoptic intubating stylet instrument for oral fiberoptic endotracheal intubation comprising in combination:

an elongate malleable stylet having a forward tip end, a rearward end, and a central longitudinal portion; said stylet capable of being manually formed to pass through the mouth and into the larynx of a particular patient into which an endotracheal tube is to be placed;

tube and bundle attachment and positioning means movably mounted on said stylet having an exterior configured to removably engage the rearward end of an endotracheal tube and releasably maintain the endotracheal tube in a surrounding condition on said stylet and an interior configured to receive and adjustably position a fiberoptic bundle;

a flexible endotracheal tube having a rearward end removably engaged on said tube and bundle attachment and positioning means, an interior diameter surrounding said stylet when engaged thereon, and a forward tip end;

said tube and bundle attachment and positioning means being selectively movable on said stylet for adjustably positioning and maintaining said forward tip end of said endotracheal tube relative to said forward tip end of said stylet; and a fiberoptic scope having viewing means connected at a rearward end and an elongate thin flexible fiberoptic bundle which transmits light and visual images extending forwardly therefrom and terminating in a tip end and having a midsection therebetween, said fiberoptic bundle passing slidably through said tube and bundle attachment and positioning means; and said tube and bundle attachment and positioning means being engaged with said fiberoptic bundle to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

9. The fiberoptic intubating stylet instrument according to claim 8 in which said stylet has a handle portion at said rearward end configured to receive the hand of an operator.

10. The fiberoptic intubating stylet instrument according to claim 8 in which said tube and bundle attachment and positioning means comprises a resilient member having a central aperture frictionally and slidably engaged on the exterior of said stylet to allow said endotracheal tube engaged thereon to slide longitudinally relative thereto.

11. The fiberoptic intubating stylet instrument according to claim 10 in which said resilient member has an exterior surface configured to frictionally engage either the rearward end of said endotracheal tube or a standard endotracheal tube connector installed in the rearward end of an endotracheal tube, and to allow disengagement and disconnection of said endotracheal tube or said endotracheal tube having a standard endotracheal tube connector installed in the rearward end thereof upon the application of sufficient axial force relative to one another.

12. The fiberoptic intubating stylet instrument according to claim 8 in which said tube and bundle positioning means comprises a resilient member having a central aperture through which said fiberoptic bundle passes and is frictionally and slidably engaged therewith to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

13. A medical instrument for use in oral fiberoptic endotracheal intubation to releasably support an endotracheal tube and the fiberoptic bundle of a fiberoptic scope and facilitate insertion of both the endotracheal tube and fiberoptic bundle into the larynx of a patient, the instrument comprising:

an elongate malleable stylet having a forward tip end, a rearward end, and a central longitudinal portion; said stylet capable of being manually formed to pass through the mouth and into the larynx of a particular patient into which an endotracheal tube is to be placed;

endotracheal tube attachment and positioning means movably mounted on said stylet configured to removably receive and engage the rearward end of an endotracheal tube of the type having an interior and exterior diameter, a rearward end, and a forward tip end, and releasably maintain the endotracheal tube in a surrounding condition on said stylet;

said endotracheal tube attachment and positioning means being selectively movable on said stylet for adjustably positioning and maintaining said forward tip end of said endotracheal tube relative to said forward tip end of said stylet; and a fiberoptic bundle positioning means connected with said endotracheal tube attachment and positioning means configured to receive and adjustably position a fiberoptic bundle;

a fiberoptic scope having viewing means connected at a rearward end and an elongate thin flexible fiberoptic bundle which transmits light and visual images extending forwardly therefrom and terminating in a tip end and having a midsection therebetween, said fiberoptic bundle passing slidably through said fiberoptic bundle positioning means; and said fiberoptic bundle positioning means being engaged with said fiberoptic bundle to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

14. The medical instrument according to claim 13 in which said endotracheal tube attachment and positioning means and said fiberoptic bundle positioning means comprises a resilient member having a first aperture frictionally and slidably engaged on the exterior of said stylet to allow said endotracheal tube engaged thereon to slide longitudinally relative thereto; and a second aperture extending through said resilient member defining said fiberoptic bundle positioning means and through which said fiberoptic bundle passes and is frictionally and slidably engaged to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

15. The medical instrument according to claim 14 in which said resilient member has an exterior surface configured to frictionally engage either the rearward end of said endotracheal tube or a standard endotracheal tube connector installed in the rearward end of an endotracheal tube, and to allow disengagement and disconnection of said endotracheal tube or said endotracheal tube having a standard endotracheal tube connector installed in the rearward end thereof upon the application of sufficient axial force relative to one another.

16. The medical instrument according to claim 13 in which said stylet has a handle portion at said rearward end configured to receive the hand of an operator.

17. The medical instrument according to claim 16 in which said handle portion comprises a generally cylindrical handle having a forward end, a rearward end, and a central longitudinal bore;

said fiberoptic bundle positioning means is disposed at the rearward end of said handle;

a tubular telescoping fiberoptic scope support arm on said handle having releasable mounting means at an outer end for releasably receiving and mounting said fiberoptic scope thereon; and said stylet comprises an elongate curvilinear hollow tubular stylet having a rearward end secured to said handle, a forward tip end, and a longitudinal channel extending therethrough coextensive with said handle central bore;

said handle central bore, said fiberoptic positioning means, and said longitudinal channel being sized to allow said fiberoptic bundle to pass slidably therethrough.

18. The medical instrument according to claim 17 in which said tubular telescoping fiberoptic scope support arm is selectively adjustable in length along its longitudinal axis and said releasable mounting means at the outer end thereof is rotatable about said longitudinal axis.

19. The medical instrument according to claim 17 in which said endotracheal tube attachment and positioning means comprises a resilient member having a central aperture frictionally and slidably engaged on the exterior of said stylet to allow said endotracheal tube engaged thereon to slide longitudinally relative thereto upon the application of sufficient axial force relative to one another.

20. The medical instrument according to claim 19 in which said resilient member has an exterior surface configured to frictionally engage either the rearward end of said endotracheal tube or a standard endotracheal tube connector installed in the rearward end of an endotracheal tube, and to allow disengagement and disconnection of said endotracheal tube or said endotracheal tube having a standard endotracheal tube connector installed in the rearward end thereof upon the application of sufficient axial force relative to one another.

21. The medical instrument according to claim 17 in which said fiberoptic bundle positioning means comprises a resilient member having a central aperture through which said fiberoptic bundle passes and is frictionally and slidably engaged therewith to allow said fiberoptic bundle to slide relative thereto when sufficient axial force is applied to said fiberoptic bundle for adjustably positioning and maintaining said tip end of said fiberoptic bundle relative to said forward tip ends of said stylet and said endotracheal tube.

* * * * *